United States Patent
Branecky et al.

(10) Patent No.: US 10,132,770 B2
(45) Date of Patent: Nov. 20, 2018

(54) FLAME ROD ANALYSIS SYSTEM

(75) Inventors: Brian T. Branecky, Oconomowoc, WI (US); Brian C. Dolder, Schererville, IN (US); Charles J. Koehler, III, Milwaukee, WI (US)

(73) Assignee: A. O. SMITH CORPORATION, Milwaukee, WI (US)

( * ) Notice: Subject to any disclaimer, the term of this patent is extended or adjusted under 35 U.S.C. 154(b) by 2560 days.

(21) Appl. No.: 12/467,091

(22) Filed: May 15, 2009

(65) Prior Publication Data

US 2010/0291494 A1  Nov. 18, 2010

(51) Int. Cl.
  *G01N 27/20* (2006.01)
  *G01N 27/04* (2006.01)
  *F23N 5/14* (2006.01)

(52) U.S. Cl.
  CPC ............ *G01N 27/20* (2013.01); *F23N 5/143* (2013.01); *G01N 27/041* (2013.01); *F23N 2029/12* (2013.01); *F23N 2029/22* (2013.01); *F23N 2031/10* (2013.01)

(58) Field of Classification Search
  USPC .................. 431/12, 18, 25, 89, 90, 42–48
  See application file for complete search history.

(56) References Cited

U.S. PATENT DOCUMENTS

| | | | |
|---|---|---|---|
| 3,266,026 A * | 8/1966 | Plambeck | 431/13 |
| 4,034,235 A | 7/1977 | Wade | |
| 4,088,984 A | 5/1978 | Muramoto et al. | |
| 4,113,419 A * | 9/1978 | Cade | 431/78 |
| 4,461,615 A | 7/1984 | Inoue | |
| 4,494,924 A | 1/1985 | Tanaka et al. | |
| 4,527,125 A | 7/1985 | Miyanaka et al. | |
| 4,710,125 A | 1/1987 | Nakamura et al. | |
| 4,672,324 A * | 6/1987 | van Kampen | 307/653 |
| 4,965,048 A * | 10/1990 | Ogasawara | G01N 30/68 422/54 |
| 4,972,324 A | 11/1990 | Tanaka | |
| 4,984,981 A | 1/1991 | Pottebaum | |
| 5,194,728 A * | 3/1993 | Peterson | 250/214 R |
| 5,256,057 A * | 10/1993 | Grow | 431/79 |

(Continued)

OTHER PUBLICATIONS

Vandermeer, "Flame Safeguard Controls in Multi-Burner Environments," Apr. 1998 (34 pages).

(Continued)

*Primary Examiner* — Steven B McAllister
*Assistant Examiner* — Desmond C Peyton
(74) *Attorney, Agent, or Firm* — Michael Best & Friedrich LLP (57) ABSTRACT

A flame rod analysis system, methods for determining a condition of a flame and a flame rod, and circuits for determining a condition of a flame and a flame rod. The flame rod analysis system comprises energy storage connectable to a flame rod, a pulsed source connected to the energy storage and providing a voltage pulse or a current pulse, and a buffer to allow a processor to measure a buffered voltage at various time points. Flame rod analysis systems can distinguish between various flame conditions (no flame, low flame, etc.) while simultaneously characterizing the condition of the flame rod (shorted to ground, contaminated, etc.). Some flame rod analysis systems can directly measure the resistance of the flame rod.

21 Claims, 9 Drawing Sheets

(56) References Cited

U.S. PATENT DOCUMENTS

| | | | |
|---|---|---|---|
| 5,347,982 A * | 9/1994 | Binzer et al. | 126/503 |
| 5,439,374 A | 8/1995 | Jamieson | |
| 5,472,336 A | 12/1995 | Adams et al. | |
| 5,538,416 A * | 7/1996 | Peterson et al. | 431/46 |
| 5,722,822 A | 3/1998 | Wilson et al. | |
| 6,059,195 A | 5/2000 | Adams et al. | |
| 6,084,518 A | 7/2000 | Jamieson | |
| 6,354,830 B1 | 3/2002 | de Nanclares | |
| 6,356,199 B1 * | 3/2002 | Niziolek et al. | 340/579 |
| 6,794,771 B2 * | 9/2004 | Orloff | 307/117 |
| 6,985,080 B2 | 1/2006 | Kociecki et al. | |
| 7,088,253 B2 | 8/2006 | Grow | |
| 7,353,140 B2 * | 4/2008 | Daw et al. | 702/182 |
| 2006/0257802 A1 * | 11/2006 | Chian et al. | 431/18 |

OTHER PUBLICATIONS jimtrade.com, "Gas Burners Flame Rod Detectors," [Retrieved from the Internet] [Online] Available May 1, 2006, at: URL < http://web.archive.org/web/20060501201220/http://articles.jimtrade.com/1/20.htm> printed Apr. 21, 2010 (3 pages).

Gayesco, LLC, "Flame Rods," [Retrieved from the Internet] [Online] Available May 9, 2008 at: URL < http://waybackmachine.org/web/20080509075438/http://www.gayesco.com/flame_rods.htm> printed on Apr. 21, 2010 ( 3 pages).

Office Action from the Canadian Intellectual Property Office for Application No. 2703681 dated Mar. 30, 2017 (3 pages).

Office Action from the Mexican Patent Office for Application No. MX/A/2010/005347 dated Dec. 2, 2013 (English Translation, 2 pages).

* cited by examiner

FLAME ROD ANALYSIS SYSTEM

FIELD OF THE INVENTION

The invention relates to systems, circuits, and methods for determining aspects of a flame rod. By determining aspects of a flame rod, it is possible to monitor the quality of a flame that may be present in a residential, commercial, or industrial burner. Such burners may be present in residential water heaters and furnaces, for example. Such burners also may be present in industrial boilers and dryers.

BACKGROUND

Burners ignite a fuel, such as natural gas or heating oil to produce heat. Modern burners typically have one or more sensors capable of monitoring the presence of a smaller ignition flame (e.g., a pilot light) as well as the larger flame that produces the heat. A variety of sensors are known, and they range in functionality (and price) as the use of the burner dictates. For example, high-end flame sensors may analyze the performance of the flame spectroscopically, and alert engineers or service technicians when the burner is not functioning optimally.

Many burners rely on flame rectification to sense the presence of a flame. In flame rectification an AC signal is sent to two electrodes contacted by the flame. Because the current from one half of the AC cycle is preferentially conducted through the flame, the AC signal is rectified to produce a noisy DC voltage. Thus, by observing a heavily-filtered DC voltage, it is possible to determine if the flame is present. If the DC voltage falls below a pre-determined value, the sensor assumes that the flame is out, and a valve shuts off the fuel flow. Flame rectification cannot distinguish between a high-resistance flame and no flame, however, because either condition results in a DC voltage below the acceptable level.

Because of the harsh environment inside the flame, the electrodes for flame rectification must be fabricated from high temperature alloys, such as kanthol, or ceramic material. These electrodes, intended for exposure to flames, are known generally as flame rods. Flame rods are available from a number of manufacturers including, but not limited to, Honeywell Inc. (Golden Valley, Minn.). In many embodiments, the burner or pilot light assembly is the second electrode needed for flame rectification, thus, typically, only one flame rod is necessary to monitor a flame with flame rectification.

Over time, flame rods develop a layer of corrosion, soot, carbonization, contamination, etc. This contamination layer may negatively affect the function of the flame rod by increasing the resistance of the flame rod. As the contamination builds up, the observed DC voltage will decrease to the point that a flame-out (no flame) event is registered. In many cases, the flame-out event will trigger an unnecessary shut-down of the burner. To avoid unnecessary shut downs, flame rods must be serviced regularly to verify that they do not have a contamination layer that will trigger a flame-out event.

SUMMARY

Accordingly, there is a need for improved systems, circuits and methods of monitoring an aspect of a flame rod. In particular, it would be advantageous if the systems, circuits and method were capable of monitoring the flame rod for contamination while being able to distinguish a flame rod short from a low-resistivity flame as well as being able to distinguish no flame from a high resistivity flame.

In one embodiment, the invention provides a system for analyzing an aspect of a flame rod. The system comprises energy storage, a pulsed source, a buffer, and a processor. The energy storage is connected to ground and connectable to the flame rod. The pulsed source is connected to the energy storage and provides a voltage pulse or a current pulse. The buffer is connected to the energy storage, and is connectable to the flame rod. The buffer buffers a voltage on the energy storage and the flame rod. The processor is connected to the buffer and the processor determines a first buffered voltage and a second buffered voltage after the pulsed source provides a voltage pulse or a current pulse. The processor additionally produces a first flag based on the first buffered voltage and a second flag based on the second buffered voltage.

In another embodiment, the invention provides a flame rod analysis circuit comprising a capacitor, a transistor switch, and an operational amplifier. The capacitor has a first terminal and a second terminal, wherein the first terminal is connectable to a flame rod and the second terminal connectable to ground. The transistor switch has a source, a drain, and a gate. The source is connected to a positive voltage, the drain is connected to the first terminal, and the gate is connectable to a signal. The operational amplifier has a positive terminal, a negative terminal, and an output. The positive terminal is connected to the first terminal, the negative terminal is connected to the output, and the output is connectable to a processor.

In another embodiment, the invention provides a method for analyzing an aspect of a flame rod connected to a pulsed source, energy storage connected to ground, and a buffered processor capable of determining a voltage on the flame rod and the energy storage. The method comprises contacting the flame rod with a flame, providing a voltage pulse or a current pulse to the flame rod and the energy storage, determining a first voltage on the flame rod and the energy storage at a first time, determining a second voltage on the flame rod and the energy storage at a second time, producing a first flag based on the first voltage, and producing a second flag based on the second voltage.

In another embodiment, the invention provides a system for determining the resistance of a flame rod, including a reference resistor, a pulsed voltage source, a buffer, and a processor. The reference resistor has a known resistance and is connectable to the flame rod. The pulsed voltage source is connected to the reference resistor and provides a voltage pulse of a known magnitude. The buffer is connected to the reference resistor and the processor, and is connectable to the flame rod. The buffer buffers a voltage between the reference resistor and the flame rod so that the processor can measure the buffered voltage. The processor determines a peak voltage between the reference resistor and the flame rod when the voltage pulse is provided by the pulsed voltage source. The processor may additionally determine a flame voltage between the reference resistor and the flame rod in the absence of a voltage pulse provided by the pulsed voltage source. The processor may produce a flag when the peak voltage exceeds a threshold voltage. The processor may determine the resistance of the flame rod based upon the resistance of the reference resistor, the magnitude of the voltage pulse, the peak voltage, and the flame voltage.

In another embodiment, the invention provides for a flame rod resistance measuring circuit comprising a reference resistor having a first terminal and a second terminal, the second terminal being connectable to the flame rod, a transistor switch having a source, a drain, and a gate, the source being connected to a positive voltage, the drain being connected to the first terminal, the gate being connectable to a signal, and an operational amplifier having a positive terminal, a negative terminal, and an output, the positive terminal connected to the first terminal, the negative terminal connected to the output, and the output connectable to a processor. The flame rod measuring circuit may additionally comprise a processor and an indicator.

In another embodiment, the invention provides for a method for determining excessive resistance through a flame rod connected to a reference resistor of known resistance, a pulsed voltage source, and a buffered processor capable of determining a voltage between the flame rod and the reference resistor. The method comprises providing a voltage pulse of known magnitude, determining a peak voltage between the reference resistor and the flame rod during the voltage pulse, and comparing the peak voltage to a threshold value. The method my additionally comprise determining a flame voltage between the reference resistor and the flame rod in the absence of the voltage pulse, and determining the resistance of the flame rod based upon the resistance of the reference resistor, the magnitude of the voltage pulse, the peak voltage, and the flame voltage.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof encompass both direct and indirect mountings, connections, supports, and couplings. Further, "connected" and "coupled" are not restricted to physical or mechanical connections or couplings.

Figure 1:
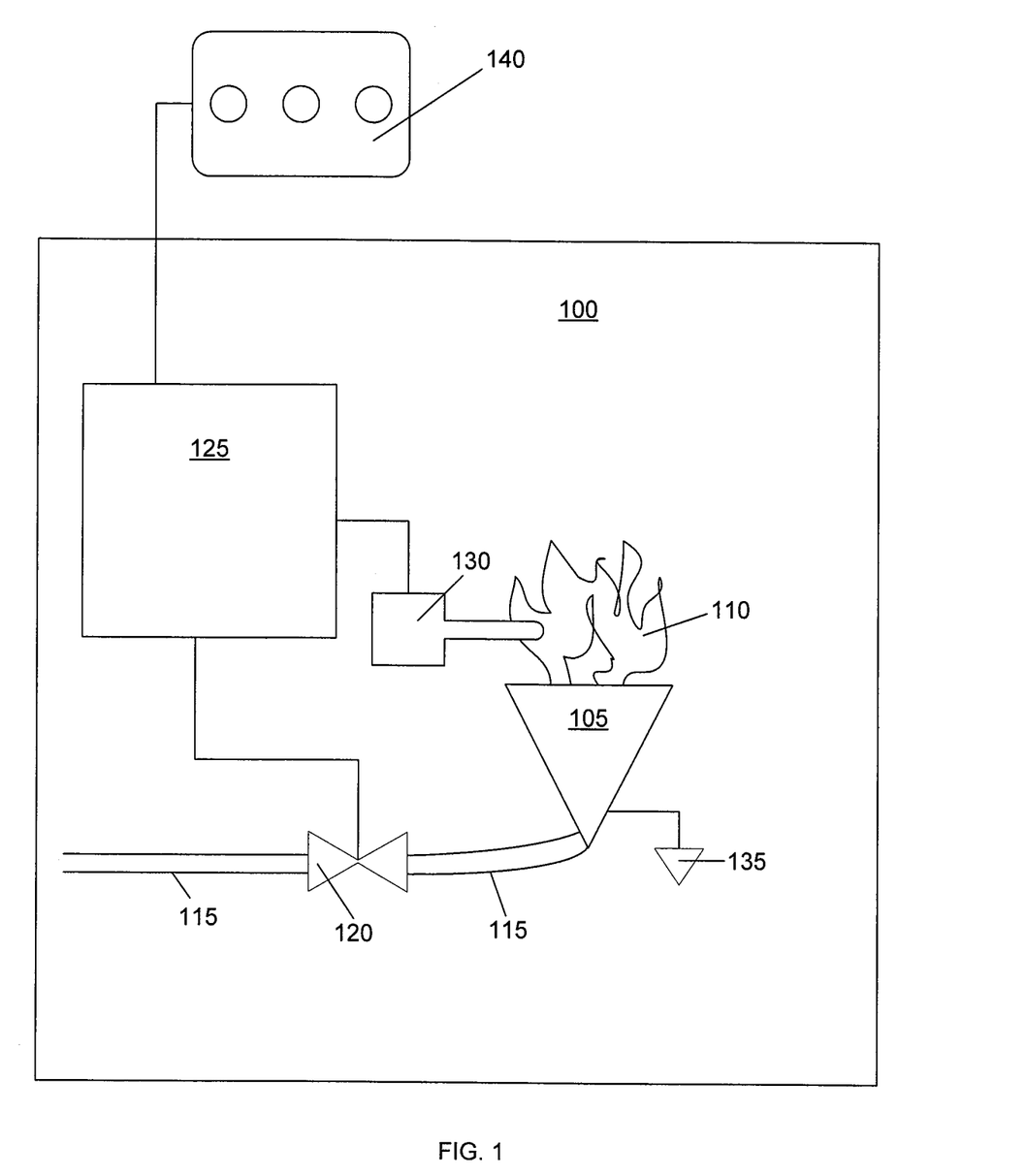
FIG. 1 is a schematic diagram of a burner unit using a flame rod to determine an aspect of the flame.

A generalized burner unit 100 that may be found in a natural-gas-fueled appliance, for example, is shown in FIG. 1. The appliance can be a residential water heater, for example. Burner 105 produces flame 110 which allows natural gas to be combusted in a controlled fashion to produce thermal energy to heat a tank of water (not shown). Burner 105 is typically fed by fuel line 115 which is connected to a source of gas, such as a municipal gas line (not shown). Typically, fuel line 115 may be interrupted by shut off valve 120, which allows one or more safety systems to halt the flow of the natural gas to burner 105 in the event that flame 110 is extinguished. Other means of fueling burner 105 are known, as fuel line 115 may supply heating oil, for example.

Burner unit 100 may have one or more flame analysis systems 125 to enable burner unit 100 to monitor the presence of flame 110. In the event that flame 110 is extinguished, flame analysis system 125 will signal shut off valve 120 to close, thus halting the flow of fuel to burner 105. Prior art systems typically use a form of flame rectification (discussed above) that involves positioning flame rod 130 in flame 110 while burner 105 is attached to ground 135. In prior art systems, an AC signal is presented to flame rod 130, and a rectified DC voltage is observed to verify presence of flame 110. When the rectified DC voltage falls below a threshold, it is assumed that flame 110 has been extinguished and shut off valve 120 is closed. Nonetheless, many prior art systems cannot distinguish between a flame 110 having high resistance, flame rod 130 being contaminated, and flame 110 being extinguished.

In contrast to the prior art, the invention described herein allows burner unit 100 to successfully halt the flow of fuel to burner 105 in the event that flame 110 is extinguished, but without the need to rely on flame rectification. Rather flame analysis systems 125 of the invention rely on modeling flame 110 as a negative current source. Flame analysis systems 125 of the invention can still monitor flame rod 130 to determine the condition of flame 110, however, flame analysis system 125 of the invention can distinguish between flame 110 having high resistance, flame rod 130 being contaminated, and flame 110 being extinguished. Because flame analysis systems 125 of the invention allow for the determination of various states of flame 110 and flame rod 130, it is advantageous to additionally incorporate alert 140 in some embodiments utilizing flame analysis systems of the invention. Alert 140 may comprise a series of light emitting diodes, for example, that can signal to a consumer or service technician the state of burner unit 100.

Figure 2:
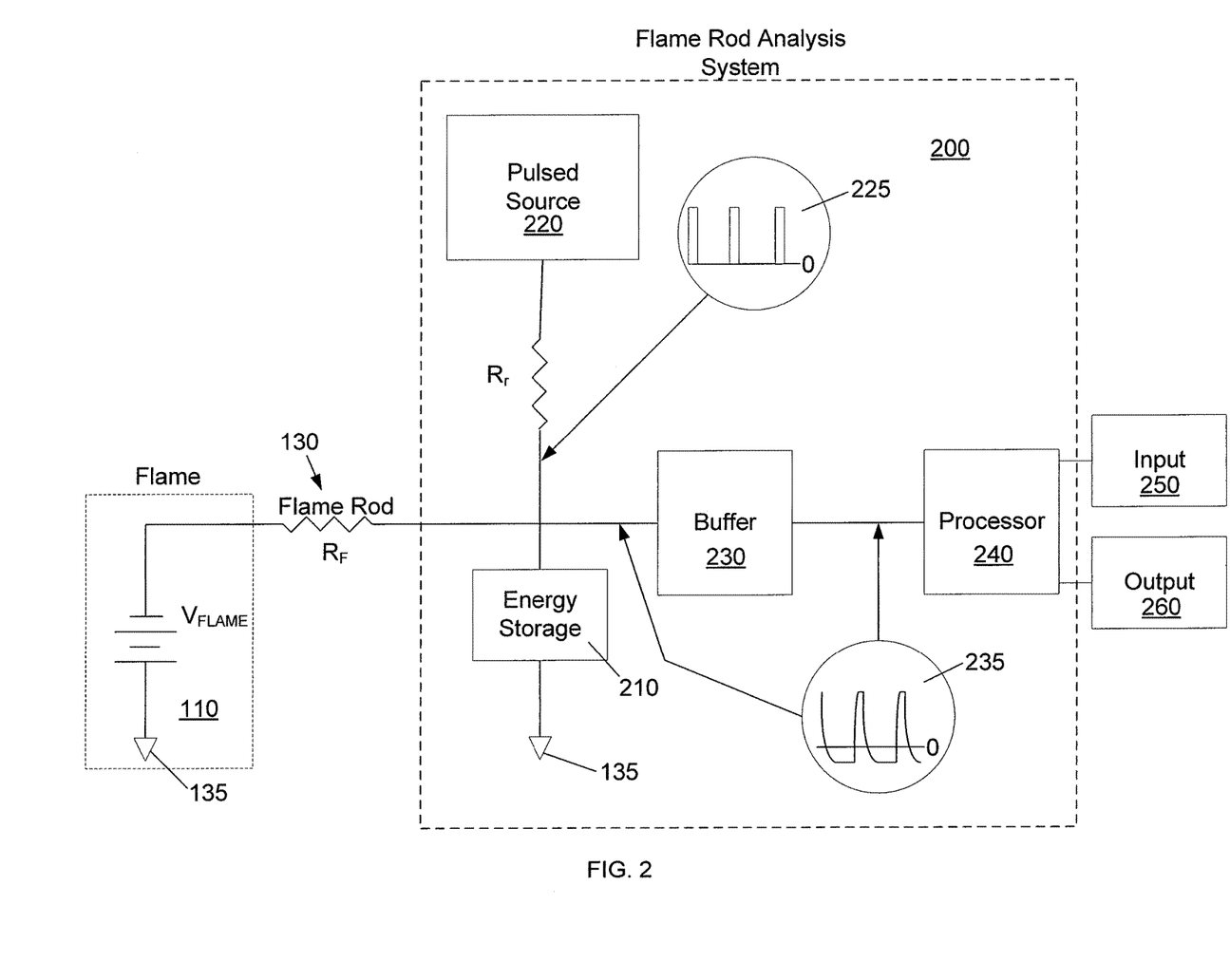
FIG. 2 is an embodiment of a system for analyzing an aspect of a flame rod.

An embodiment of a flame analysis system 200 of the invention is shown in FIG. 2. Flame analysis system 200 comprises energy storage 210, pulsed source 220, buffer 230, and processor 240. Energy storage 210 (e.g., a capacitor or inductor) is connected to ground and pulsed source 220. Typically, energy storage 210 is additionally connected to flame rod 130 and buffer 230. Buffer 230 is additionally connected to processor 240. Buffer 230 serves to buffer the voltage observable on energy storage 210 from current spikes. Buffer 230 also assures that the energy in energy storage 210 can only decay through flame rod 130. Flame analysis system 200 may comprise additional components (e.g., filters) that are not shown, but are useful to produce the desired response in flame analysis system 200, and to protect flame analysis system 200 from current spikes. Processor 240 determines a voltage on the energy storage at various times, as described below. Processor 240 may optionally have a processor input 250 and a processor output 260.

As understood by one skilled in the art, when referencing a parameter, such as voltage, resistance, current, etc., it is not necessary to determine an actual value for voltage, resistance, current, etc. to determine the condition of the flame rod or the flame. For example, it is possible to compare a signal value representative of a voltage, resistance, current, etc. to a comparison value, or another signal value corresponding to another voltage, resistance, current, etc. of interest to determine a condition of the flame rod or the flame. Where it is stated that processor 240 determines voltage, resistance, current, etc., the statement is intended to include embodiments in which processor 240 determines actual values of voltage, resistance, current, etc., and embodiments in which processor 240 determines signal values representative of voltage, resistance, current, etc.

Pulsed source 220 typically provides a voltage pulse 225 at regular intervals to energy storage 210. (In some embodiments pulsed source 220 provides a current pulse to energy storage 210.) Assuming flame rod 130 has not been grounded, voltage pulse 225 will result in energy storage 210 becoming charged. Over some period of time, the energy stored in energy storage 210 will drain through flame 110 to ground 135. However, because flame 110 is effectively a negative current source, flame 110 will ultimately pull energy storage 210 down, typically below ground 135. This behavior is illustrated by decay waveform 235 present between buffer 230 and processor 240. That is, when flame 110 and flame rod 130 are working properly, each voltage pulse 225 results in the voltage on energy storage 210 rising to nearly the peak of voltage pulse 225, then decaying away, and then being pulled negative.

Figure 3:
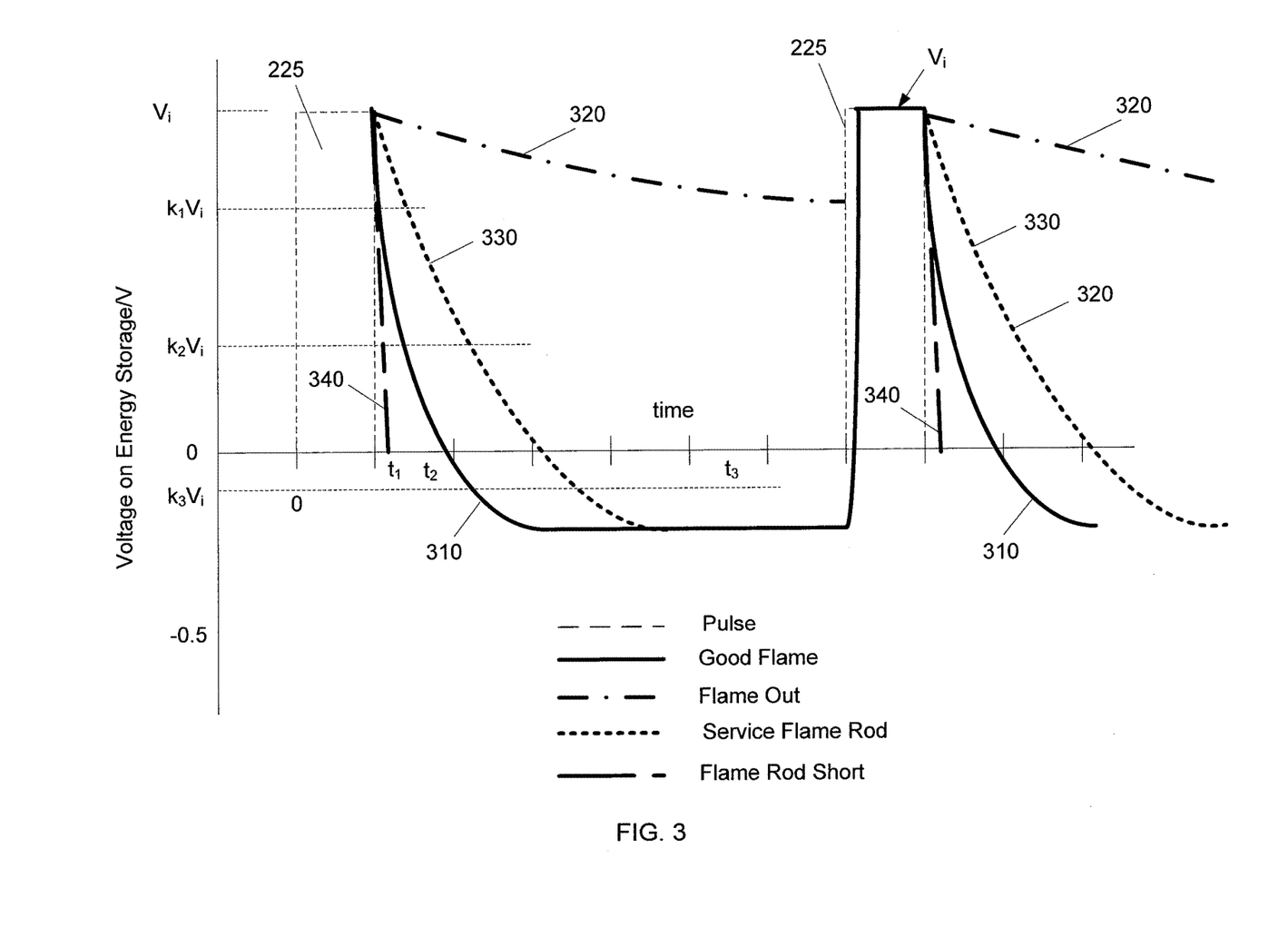
FIG. 3 depicts time dependent voltage curves that may be determined by a processor in a system for analyzing an aspect of a flame rod.

Voltage pulse 225 and decay waveform 235 are better illustrated in FIG. 3. As an example, voltage pulse 225 may be 1 V in magnitude. Generally, however, the magnitude of voltage pulse 225 will be indicated as $V_i$. In the event that flame 110 and flame rod 130 are working properly, voltage pulse 225 results in good flame waveform 310. Good flame waveform 310 decays quickly upon the termination of voltage pulse 225. Good flame waveform 310 passes through 0 V, and is ultimately pulled to a negative value until the subsequent voltage pulse 225 is delivered to energy storage 210. In the event that flame rod 130 has become grounded, for example by contacting the grounded burner, all of voltage pulse 225 will be transferred to ground, and there will be no voltage on energy storage 210, thus no waveform. A flame short may be alternatively visualized as an instantaneous return to ground upon termination of the voltage pulse or current pulse, e.g., flame short waveform 340.

In the event that flame 110 has gone out, the voltage on energy storage 210 will decay slightly after voltage pulse 225 because of the natural decay through energy storage 210. However, in the event of a flame out, energy storage 210 will typically stay charged until the next voltage pulse 225. The resulting waveform, depicted as flame out waveform 320 in FIG. 3, decays slightly from the magnitude of voltage pulse 225 but does not approach ground.

In the event that flame rod 130 has become contaminated or corroded, the resistance ($R_F$) of flame rod 130 to the negative current produced by flame 110 increases. Because of this increased resistance, the voltage on energy storage 210 takes longer to decay to a negative value, thus producing service flame rod waveform 330. Of course, as flame rod 130 becomes more contaminated or corroded, the rate of decay of service flame rod waveform 330 will decrease.

In some embodiments, it may be beneficial to collect all of waveform 235 resulting from the decay of voltage on energy storage 210 through flame rod 130. Techniques such as logarithmic approximation or polynomial fitting may be used to uniquely determine the shape of waveform 235 with suitable processors.

In other embodiments, waveforms 235 may be adequately characterized by making voltage measurements at predetermined intervals after voltage pulse 225 is sent to energy storage 210, and comparing the voltage measurements to $k_x V_i$ wherein $k_x$=−1 to 1, and $V_i$ is the magnitude of the voltage pulse. The sequence of measurements, as identified with subscripts, is meant to aid one of skill in the art in interpreting the waveforms presented in FIG. 3, and is not meant to indicate the necessity of a particular measurement prior to a subsequent measurement. Furthermore, numerical subscripts for measurements of time and voltage, or mathematical functions do not indicate an order. That is, measurement three need not follow measurement two, nor does measurement three indicate the existence of measurement two.

In one embodiment, flame analysis system 200 will record two buffered voltage measurements, $V_1$ and $V_3$ at times $t_1$ and $t_3$, respectively, allowing processor 240 to produce a first flag indicative of a flame rod short by comparing $V_1$ to $k_1 V_i$ and a second flag indicative of no flame by comparing $V_3$ to $k_3 V_i$. In another embodiment, waveform 235 may be better characterized by making three buffered voltage measurements $V_1$, $V_2$, and $V_3$ at times $t_1$, $t_2$, and $t_3$, respectively, allowing processor 240 to produce a first flag indicative of a flame rod short by comparing $V_1$ to $k_1 V_i$, a second flag indicative of no flame by comparing $V_3$ to $k_3 V_i$, and a third flag indicative of a contaminated flame rod by comparing by comparing $V_2$ to $k_2 V_i$. The approximate locations of times $t_1$, $t_2$, and $t_3$ are shown in FIG. 3.

Typically, first buffered voltage measurement, $V_1$, at time $t_1$ indicates the presence of a short between flame rod 130 and ground 135. That is, if flame rod 130 has shorted to ground, $V_1$ will be smaller than a first multiplier, $k_1$, of voltage pulse 225, e.g., $V_1 < k_1 V_i$. If $V_1 < k_1 V_i$, processor 240 produces a first flag indicating a flame rod 130 short. However if $V_1 > k_1 V_i$, the normal operable state, processor 240 does not produce a first flag. Processor 240 will typically be programmed to measure $V_1$ a short period after voltage pulse 225 is completed. In some embodiments, processor 240 may be triggered by a separate signal (not shown) that also triggers pulsed source 220 so that $V_1$ is measured at an appropriate time. Processor 240 may additionally comprise memory to allow processor 240 to store values of $V_1$ for later data collection and analysis. First multiplier, $k_1$, is less than 0.99, typically less than 0.9, more typically less than 0.8.

Typically, second buffered voltage measurement $V_3$ at time $t_3$ indicates the presence of flame 110 on flame sensor 130. That is, if flame 110 has gone out, the voltage at energy storage 210 will not be pulled down sufficiently to pass through threshold $k_3 V_i$. Multiplier $k_3$ is typically small, and may be positive or negative. In some embodiments, $k_3$=0. If $V_3 > k_3 V_i$, processor 240 produces a second flag indicative of no flame. The second flag, indicative of no flame, typically initiates a sequence by which the fuel feeding burner 105 is interrupted with shut off valve 120. However if $V_3 < k_3 V_i$, the normal operable state, processor 240 does not produce a second flag.

Typically, third buffered voltage measurement $V_2$ at time $t_2$ indicates the condition of flame rod 130. That is, if flame rod 130 has become contaminated or corroded, $V_2$ will be greater than a second multiplier, $k_2$, of voltage pulse 225, e.g., $V_2 > k_2 V_i$. If $V_2 > k_2 V_i$, processor 240 produces a third flag indicating that flame rod 130 is contaminated. However, if $V_2 < k_2 V_i$, the normal operable state, processor 240 does not produce a third flag. Second multiplier, $k_2$, is greater than 0.01, typically greater than 0.1, more typically greater than 0.2.

In other embodiments, processor 240 has memory to store the values of $V_3$. Processor 240 may be additionally configured to average the values of $V_3$ to produce an average second buffered voltage, and processor 240 may compare $V_3$ to the average second buffered voltage. Processor 240 may be programmed to produce a fourth flag, indicative of low flame, in the event that $V_3$ is greater than the average second buffered voltage. The stored values of $V_3$ may be additionally accessed for data collection and analysis.

Figure 4:
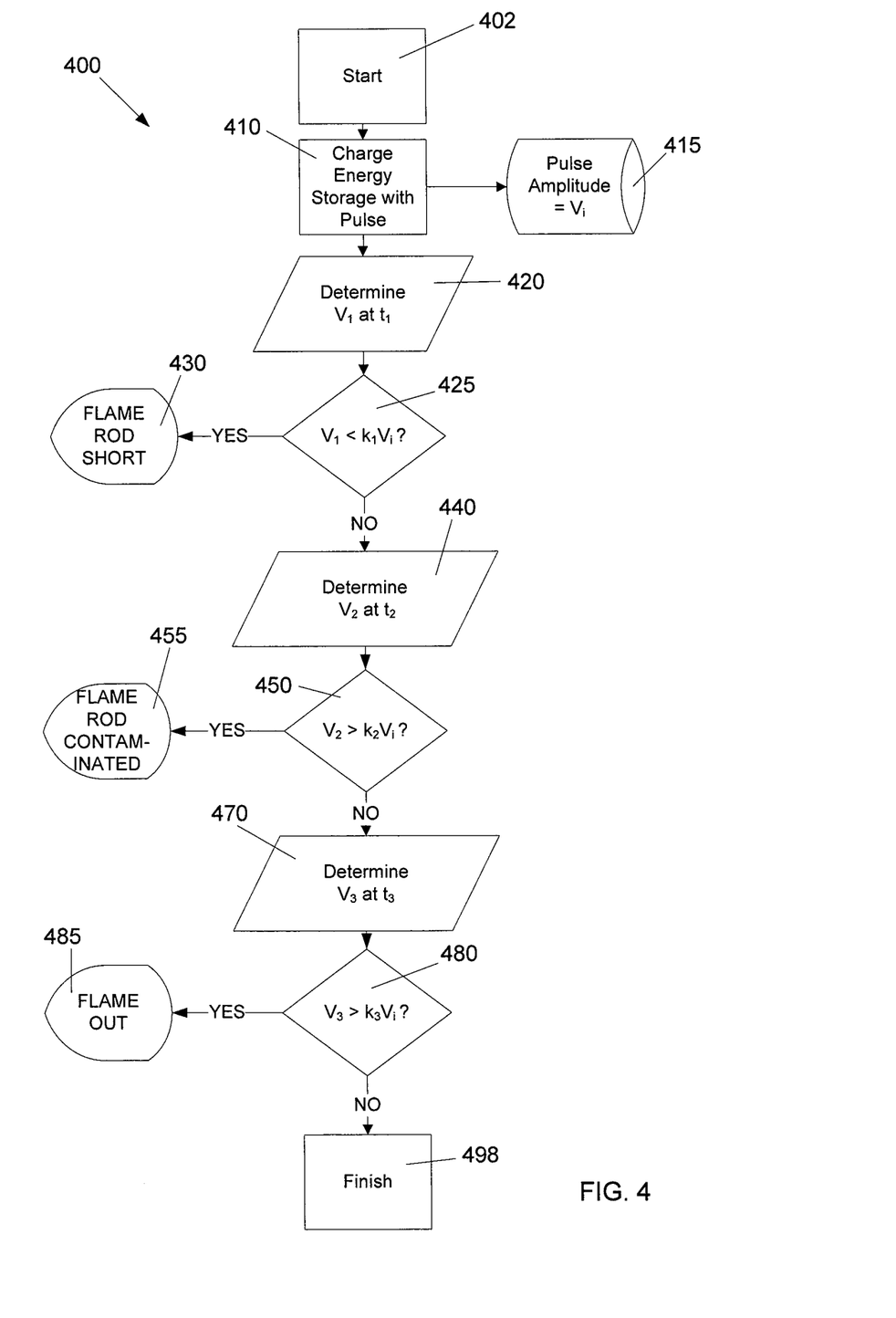
FIG. 4 is a flow chart describing an embodiment of a method for analyzing several aspects of a flame rod used to monitor a flame.

The sequence of measurements taken by flame analysis system 200 capable of producing first, second, and third flags, is depicted by flow chart 400 shown in FIG. 4. The process begins with start 402, whereby pulsed source 220 produces voltage pulse 225 (or current pulse) to charge energy storage 210 at step 410. The amplitude, $V_i$, of the voltage pulse is stored in memory at step 415 for reference, however $V_i$ need not be measured for each voltage pulse 225. Processor 240 determines $V_1$ at $t_1$ in step 420, and compares it to $k_1 V_i$ at step 425. If $V_1$ is less than $k_1 V_i$, processor 240 produces FLAME ROD SHORT flag 430, which may trigger a series of events not shown, such as terminating the flow of fuel to burner 105.

Assuming that $V_1$ is greater than $k_1 V_i$, processor 240 determines $V_2$ at $t_2$ in step 440. After determining the value of $V_2$, processor 240 compares the value of $V_2$ to $k_2 V_i$ in step 450. If $V_2$ is greater than $k_2 V_i$, processor 240 produces FLAME ROD CONTAMINATED flag 455. FLAME ROD CONTAMINATED flag 455 may trigger a series of events not shown, such as causing an LED to illuminate or producing an audible alarm.

Regardless of whether $V_2$ is greater than $k_2 V_i$, processor 240 next determines $V_3$ at $t_3$ in step 470. After determining the value of $V_3$, processor 240 compares the value of $V_3$ to $k_3 V_i$ in step 480. If $V_3$ is greater than $k_3 V_i$, processor 240 produces FLAME OUT flag 485. FLAME OUT flag 485 may trigger a series of events not shown, such as terminating the flow of fuel to burner 105.

In the event that $V_3$ is less than $k_3 V_i$, flame analysis system 200 determines that flame rod 130 and flame 110 are functioning properly, and flow chart 400 terminates with finish step 498. Processor 240 typically returns to start 402 with the introduction of a subsequent voltage pulse 225 from pulsed source 220. The time between subsequent voltage pulses 225 is greater than hundredths of a second, typically greater than tenths of a second, more typically greater than seconds.

Figure 5:
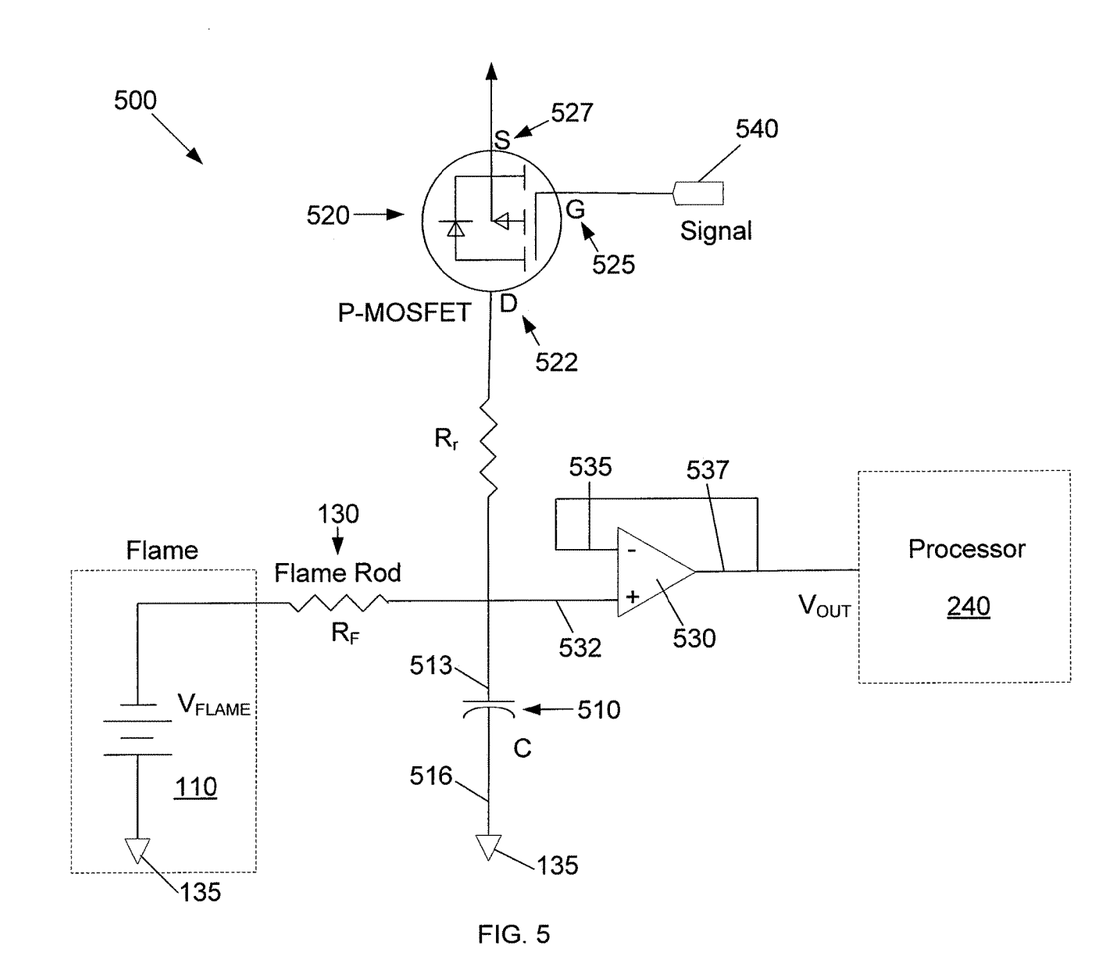
FIG. 5 is an embodiment of a flame rod analysis circuit.

Flame rod analysis circuit 500, which is an embodiment of flame analysis system 200, is shown in FIG. 5. Flame rod analysis circuit 500 comprises capacitor 510, transistor switch 520, and operational amplifier 530. Capacitor 510 has first terminal 513 and second terminal 516, wherein first terminal 513 is connectable to flame rod 130 and second terminal 516 is connectable to ground 135. Transistor switch 520 may be a p-channel MOSFET, comprising drain 522, gate 525, and source 527 as depicted in FIG. 5. Source 527 is tied to a positive voltage source, drain 522 is connected to first terminal 513, and gate 525 is connectable to a signal 540. Operational amplifier 530, having positive terminal 532, negative terminal 535, and output 537 is arranged to act as a buffer. That is, positive terminal 532 is connected to first terminal 513, while negative terminal 535 is connected to output 537. Output 537 is connectable to processor 240, and processor 240 is capable of determining voltages at various time points, as discussed above. Flame rod analysis circuit 500 may additionally comprise resistors, capacitors, diodes, and transistors as necessary to condition the signal and to protect components of flame rod circuit 500 from current surges.

As prompted by signal 540, transistor switch 520 will allow an amount of current to pass through transistor switch 520 to energize capacitor 510. Assuming flame rod 130 is in flame 110 and not grounded, the voltage on capacitor 510 will decay with time through flame rod 130 to produce a voltage waveform as described above. By measuring a buffered voltage at output 537, it is possible for processor 240 to determine voltages at various time points after voltage pulse 225 is transmitted through transistor switch 520. Because operational amplifier 530 buffers the voltage on capacitor 510, processor 240 is protected from current spikes that might damage processor 240.

Electrical components suitable for the construction of flame rod analysis circuit 500 according to invention are available from a number of suppliers, including Digi-Key electronics (Thief River Falls, Minn.). P-channel MOSFETs produced by Zetex, such as ZXMP6A13FCT-ND, are suitable for use as transistor switch 520. Operational amplifiers produced by Texas Instruments, such as TL062ID are suitable for use as operational amplifier 530. Integrated circuits produced by Freescale Semiconductor, such as MC9S08AW60CFGE, are suitable for use as processor 240. One of skill in the art may substitute other components for these components to produce different flame rod analysis circuits that are equally capable of performing the measurements described herein.

Figure 6:
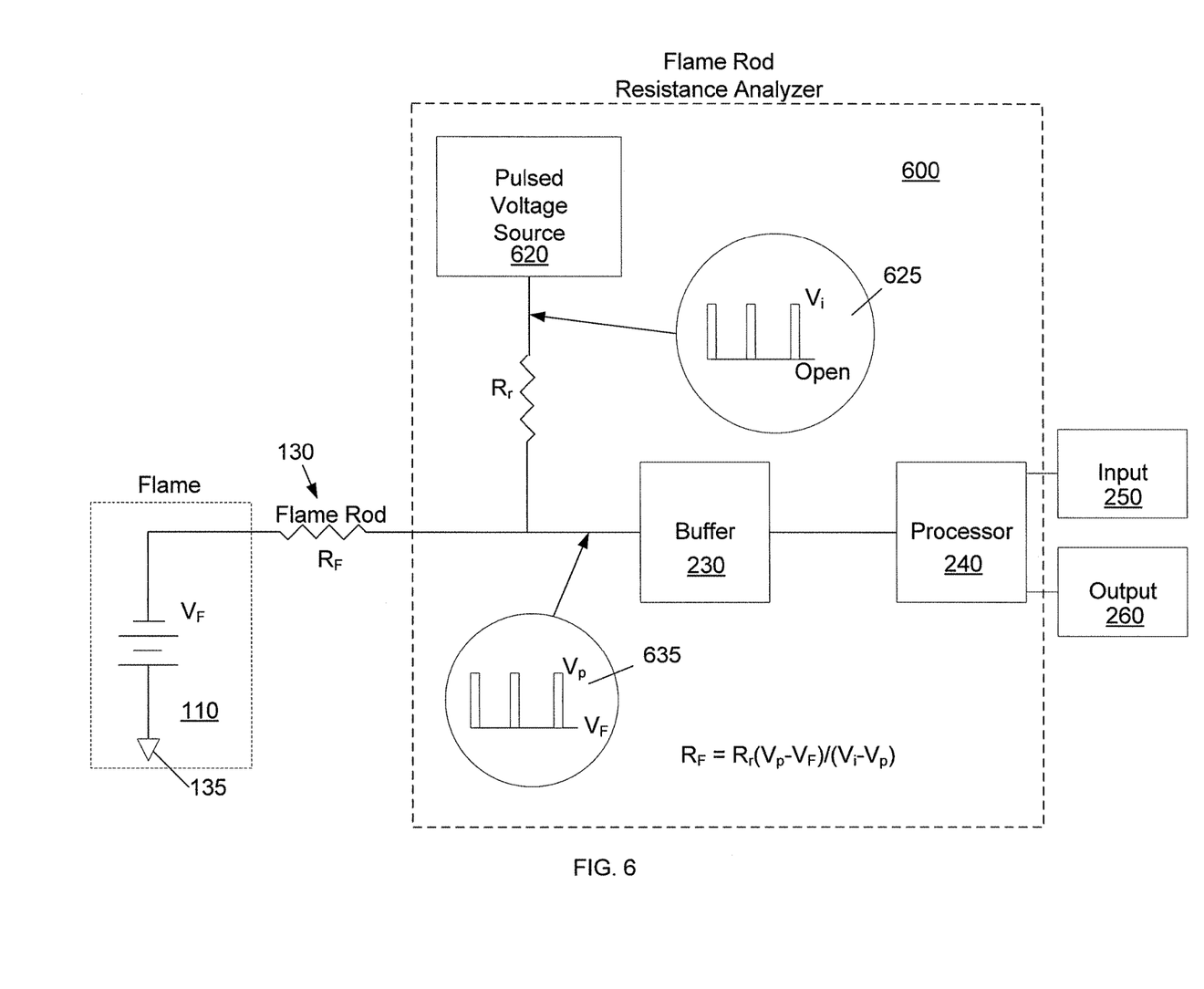
FIG. 6 is an embodiment of a flame rod resistance analyzer.

The invention additionally provides a flame rod resistance analyzer 600 for determining the resistance of a flame rod, as is shown in FIG. 6. Like flame rod analysis system 200, the technique involves the use of a pulsed source, such as pulsed voltage source 620. Pulsed voltage source 620 provides one or more pulses, as illustrated by pulsed voltage waveform 625. Each pulse has a known magnitude $V_i$. After passing through reference resistor $R_r$, the peak voltage ($V_p$) will be $V_p = V_i - R_r I$, where I is the current passing through $R_r$. Accordingly, the voltage drop over reference resistor $R_r$ produces peak voltage waveform 635 at buffer 230. Peak voltage waveform drops to $V_F$ between pulses, allowing a direct measurement of $V_F$ between pulses via buffer 230.

Assuming the circuitry is properly isolated, and buffer 230 is not drawing any current, the current, I, passing through reference resistor $R_r$ returns to ground via flame rod 130. Accordingly, $V_p = V_F + R_F I$. Thus, the resistance of flame rod 130, $R_F$, is equal to $$R_F = R_r \left( \frac{V_p - V_F}{V_i - V_p} \right)$$

Therefore by knowing $R_r$ and $V_i$, and measuring $V_p$ during voltage pulses, and $V_F$ between voltage pulses, it is possible to directly measure the resistance of the flame rod. Using this method, the processor can calculate the resistance of the flame rod, $R_F$, and compare it to a threshold resistance. Should the resistance of the flame rod, $R_F$, exceed the threshold, the processor may produce a flag.

Figure 9:
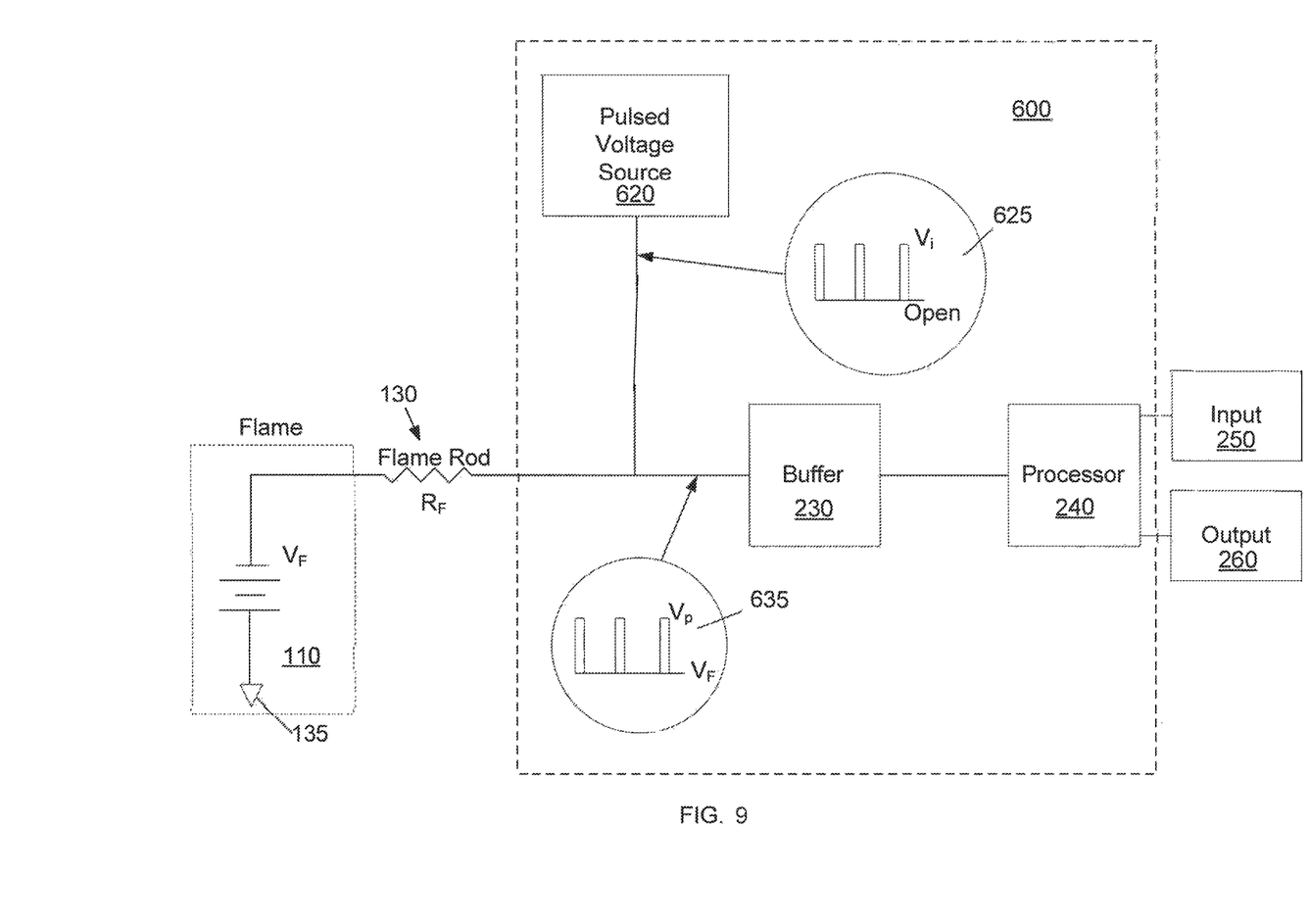
FIG. 9 is an embodiment of a flame rod resistance analyzer.

In some embodiments of flame rod resistance analyzer 600, it is not necessary to actually calculate RF because the relationship between $V_p$ and $V_F$ is sufficient to determine excessive resistance through flame rod 130 by measuring only $V_p$. For example, as the resistance of flame rod 130, $R_F$, increases, $V_p$ will approach $V_i$, assuming $V_F$ is small in magnitude. By measuring $V_p$ during the voltage pulse, and comparing $V_p$ to $V_i$, processor 240 can determine excessive resistance through flame rod 130, and produce a flag indicating excessive resistance through flame rod 130. In such embodiments, as shown in FIG. 9, the reference resistor $R_r$, may be omitted from the analyzer 600 so long as $V_p$ is able to be measured.

In some embodiments of flame rod analysis system 200 employing voltage pulses and having reference resistor $R_r$, excessive resistance through flame rod 130 can be determined by comparing $V_p$ to $V_i$, as described above. In other embodiments of flame rod analysis system 200 employing voltage pulses and having reference resistor $R_r$, the length of time between voltage pulses is sufficient that all energy stored in energy storage 210 dissipates through flame rod 130, allowing a measurement of $V_F$. See, for example, good flame waveform 310 in FIG. 3. Because it is possible to additionally measure $V_p$ during the voltage pulse 225 in flame rod analysis system 200, a direct measurement of $R_F$, can be achieved with flame rod analysis system 200 using the method outlined above. In other embodiments of flame rod analysis system 200, it may be useful to employ a switch to isolate energy storage 210 from pulsed source 220 and flame rod 130 in order to measure the resistance of the flame rod $R_F$ directly. In embodiments in which voltage measurements are taken at first and second times, or at first, second, and third times, the measurement of $V_p$ corresponds to a fourth voltage measurement, taken at fourth time. The measurement of $V_p$ may precede the measurements at first, second, and third times, however.

Figure 7:
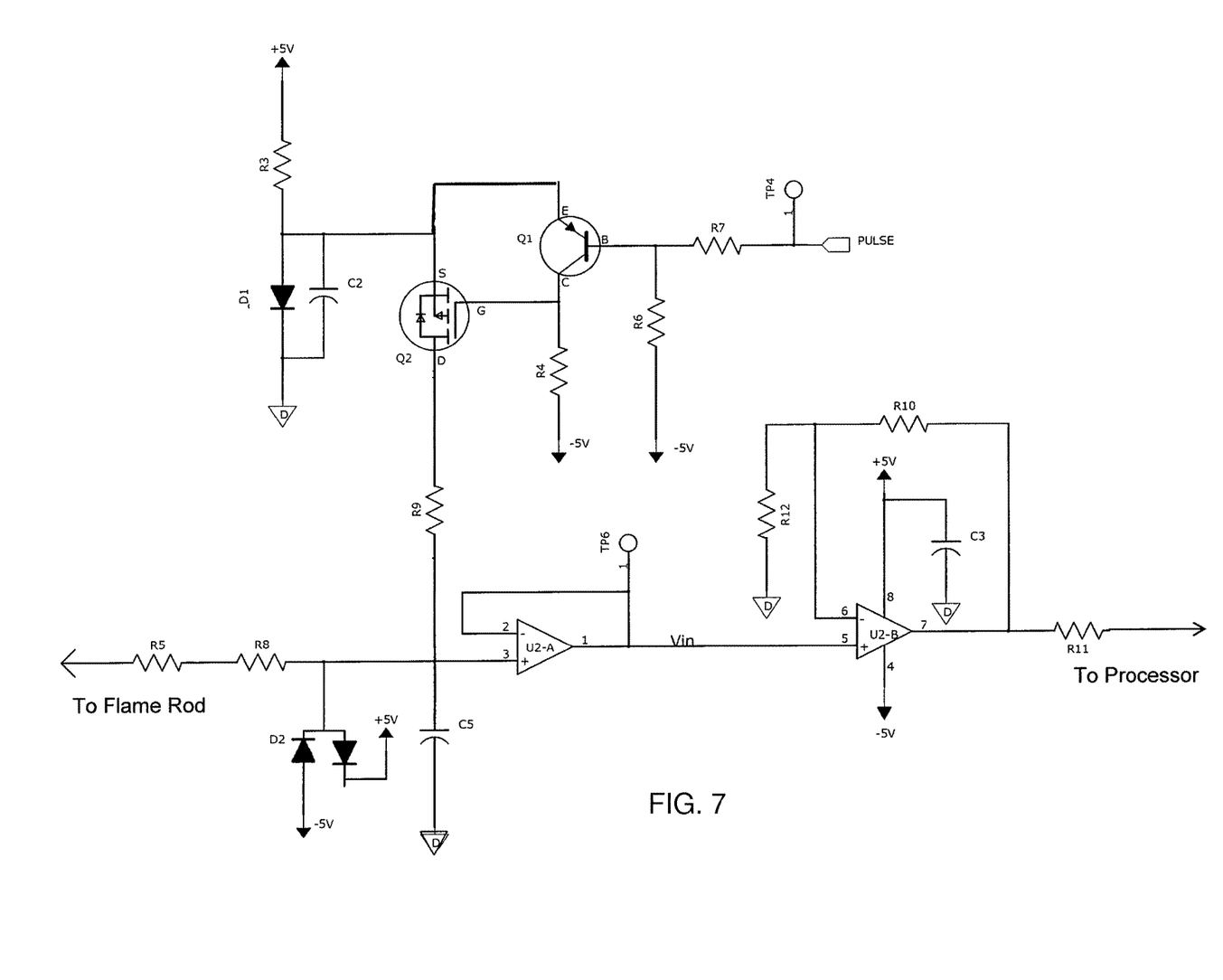
FIG. 7 is an embodiment of a flame analysis circuit, including signal isolation, signal filtering, and surge protection.

An exemplary embodiment of flame rod analysis circuit 500 is shown in FIG. 7. The embodiment in FIG. 7 comprises the same elements of flame rod analysis circuit 500 shown in FIG. 5, however the exemplary embodiment contains additional circuitry to condition the positive voltage connected to source 527, as well as circuitry to protect components of the circuit in the event that flame rod 130 becomes grounded. The embodiment shown in FIG. 7 additionally contains an amplifier to boost the voltage of the buffered voltage after operational amplifier 530.

Figure 8:
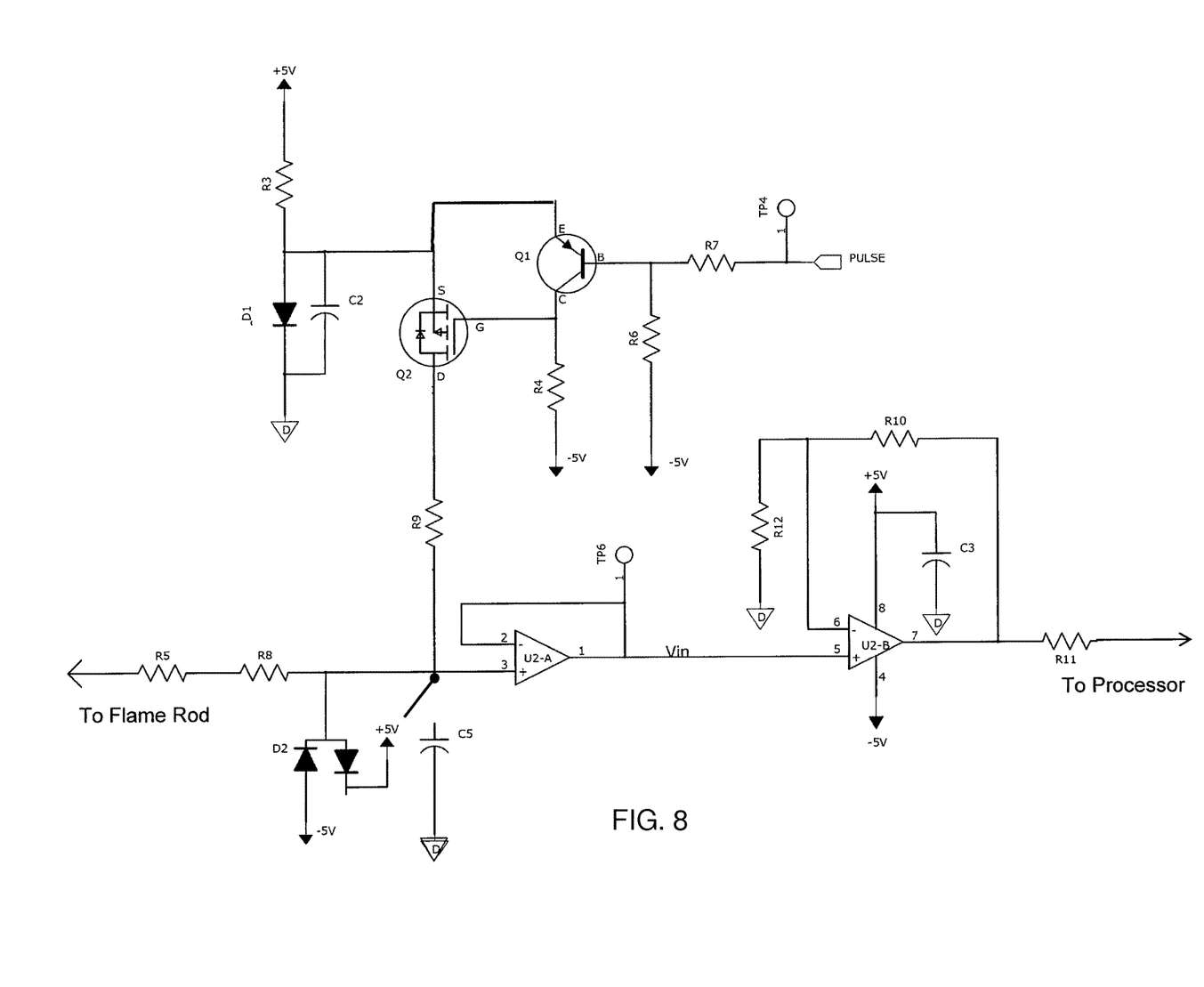
FIG. 8 is another embodiment of a flame analysis circuit, including signal isolation, signal filtering, surge protection, and energy storage isolation.

An alternative embodiment of the flame rod analysis circuit 500 is shown in FIG. 8. The embodiment of FIG. 8 contains an additional switch between capacitor 510 and the node connecting buffer 530, resistor R9, and the flame rod. The switch may be a simple toggle, however more complicated means of switching, such as a transistor, will be achievable by one of skill in the art. By isolating the capacitor, it is possible to directly measure the resistance of the flame rod assuming the magnitude of the voltage pulse originating from transistor switch 520, and the resistance of resistor R9, are known. Such a feature may be useful for trouble-shooting fault signals from a flame rod analysis system described herein.

Like FIG. 7, the embodiment of FIG. 8 contains additional circuitry to condition the positive voltage connected to source 527, as well as circuitry to protect components of the circuit in the event that flame rod 130 becomes grounded. The embodiment in FIG. 8 additionally contains an amplifier to boost the voltage of the buffered voltage after operational amplifier 530.

Thus, the invention provides, among other things, systems, circuits, and methods for determining aspects of a flame rod. Various features and advantages of the invention are set forth in the following claims.

What is claimed is:

1. A flame rod analysis circuit comprising:
a capacitor having a first terminal and a second terminal, the first terminal connectable to a flame rod, the second terminal connectable to ground;
a transistor switch having a source, a drain, and a gate, the source being connected to a positive voltage, the drain being connected to the first terminal, the gate being connected to a periodic signal source; and
an operational amplifier having a positive terminal, a negative terminal, and an output, the positive terminal connected to the first terminal, the negative terminal connected to the output, and the output connectable to a processor.

2. The flame rod analysis circuit of claim 1, further comprising a processor connected to the output, the processor determining a voltage of the output.

3. The flame rod analysis circuit of claim 2, further comprising an indicator indicating a status of the flame rod.

4. The flame rod analysis circuit of claim 1, further comprising a resistor connected from the drain to the first terminal.

5. A method for analyzing an aspect of a flame rod connected to a pulsed source, an energy storage component connected between the pulsed source and ground, and a buffered processor capable of determining a voltage on the flame rod and the energy storage, the method comprising:
contacting the flame rod with a flame;
providing a voltage pulse or a current pulse of a defined duration to the flame rod and the energy storage component,
wherein, when a flame is present and the flame rod is operating properly, the pulse charges the energy storage component,
wherein the energy storage component discharges gradually when the pulse ends, and
wherein the rate of discharge of the energy storage component is related to the flame and a condition of the flame rod;
determining a first voltage on the flame rod and the energy storage component at a first time after the pulse is provided;
determining a second voltage on the flame rod and the energy storage component at a second time after the pulse is provided;
setting a first flag based on the first voltage, wherein the first flag is indicative of a first condition of at least one of the flame and the flame rod; and
setting a second flag based on the second voltage, wherein the second flag is indicative of a second condition of at least one of the flame and the flame rod.

6. The method of claim 5, further comprising:
determining a third voltage on the flame rod and the energy storage at a third time; and
producing a third flag based on the third voltage, wherein the third flag is indicative of a third condition of at least one of the flame and the flame rod.

7. The method of claim 6, further comprising:
determining a fourth voltage on the flame rod and the energy storage at a fourth time; and producing a fourth flag based on the fourth voltage, wherein the fourth flag is indicative of a fourth condition of at least one of the flame and the flame rod.

8. The method of claim 5, further comprising comparing the first voltage to a first multiplier of the voltage pulse, and
wherein the first condition includes a flame rod short.

9. The method of claim 5, further comprising comparing the second voltage to a second multiplier of the voltage pulse, and
wherein the second condition includes a lack of flame.

10. The method of claim 6, further comprising comparing the third voltage to a third multiplier of the voltage pulse, and
wherein the third condition includes a corroded flame rod.

11. The method of claim 7, further comprising comparing the fourth voltage to a magnitude of the voltage pulse; and
wherein the fourth condition includes excessive resistance through the flame rod.

12. A flame rod resistance measuring circuit comprising:
a reference resistor having a first terminal and a second terminal, the second terminal being connectable to a flame rod;
a transistor switch having a source, a drain, and a gate, the source being connected to a positive voltage, the drain being connected to the first terminal, the gate being connected to a periodic signal source; and
an operational amplifier having a positive terminal, a negative terminal, and an output, the positive terminal connected to the second terminal, the negative terminal connected to the output, and the output connectable to a processor.

13. The flame rod resistance measuring circuit of claim 12, further comprising an indicator indicating a status of the flame rod.

14. A method for determining excessive resistance through a flame rod connected to a reference resistor of known resistance, a pulsed voltage source, and a buffered processor capable of determining a voltage between the flame rod and the reference resistor, the method comprising:
providing a voltage pulse of known magnitude;
determining a peak voltage between the reference resistor and the flame rod during the voltage pulse;
determining excessive resistance through the flame rod based upon the peak voltage.

15. The method of claim 14, further comprising:
determining a flame voltage between the reference resistor and the flame rod in the absence of the voltage pulse;
determining the resistance of the flame rod based upon the resistance of the reference resistor, the magnitude of the voltage pulse, the peak voltage, and the flame voltage.

16. The flame rod analysis circuit of claim 1, wherein a periodic signal applied to the gate of the transistor switch by the periodic signal source causes the transistor switch to open and close periodically,
wherein, when a flame is present and the flame rod is operating properly, closing the transistor switch causes the positive voltage to charge the capacitor and the capacitor discharges over a period of time when the transistor switch is opened.

17. The flame rod resistance measuring circuit of claim 12, further comprising a capacitor coupled between the second terminal of the reference resistor and ground,
wherein a periodic signal applied to the gate of the transistor switch by the periodic signal source causes the transistor switch to open and close periodically, and
wherein, when a flame is present and the flame rod is operating properly, closing the transistor switch causes the positive voltage to charge the capacitor and the capacitor discharges over a period of time when the transistor switch is opened.

18. The method of claim 5, wherein a flame rod short drains the voltage pulse such that the energy storage component is not fully charged by the voltage pulse and the first voltage of the flame rod and the energy storage component at the first time is lower than a first voltage under normal circuit operation.

19. The method of claim 5, wherein a present flame causes the energy storage component to discharge more rapidly and causes the second voltage on the flame rod and the energy storage component at the second time to be lower than a second voltage when the flame is not present.

20. The method of claim 10, wherein a corroded flame rod causes the energy storage component to discharge more slowly and causes the third voltage on the flame rod and the energy storage component at the third time to be higher than a third voltage with a non-corroded flame rod.

21. The method of claim 11, wherein excessive flame rod resistance causes the energy storage component to discharge more slowly and causes the third voltage on the flame rod and the energy storage component at the third time to be higher than a third voltage with a non-corroded flame rod.

* * * * *